(12) United States Patent
Tanahashi et al.

(10) Patent No.: US 7,799,802 B2
(45) Date of Patent: Sep. 21, 2010

(54) METHOD AND HEALTH FOOD FOR PREVENTING AND/OR ALLEVIATING PSYCHIATRIC DISORDER, AND/OR FOR EFFECTUATING SEDATION

(75) Inventors: Takao Tanahashi, Kobe (JP); Jun Yamada, Takarazuka (JP); Hiroshi Nakajima, 80-4, Emba, Makishima-cho, Uji-shi, Kyoto-fu (JP); Shu-Jian Sun, Nishinomiya (JP)

(73) Assignees: Institstute of Oriental Medical Science Inc., Osaka (JP); Hiroshi Nakajima

( * ) Notice: Subject to any disclaimer, the term of this patent is extended or adjusted under 35 U.S.C. 154(b) by 1509 days.

(21) Appl. No.: 10/949,247

(22) Filed: Sep. 27, 2004

(65) Prior Publication Data

US 2006/0030586 A1    Feb. 9, 2006

(30) Foreign Application Priority Data

Aug. 3, 2004    (JP) .............................. 2004-227227

(51) Int. Cl.
    *A61K 31/47* (2006.01)
(52) U.S. Cl. ...................................... 514/310; 514/307
(58) Field of Classification Search ................ 514/307, 514/310
    See application file for complete search history.

(56) References Cited

U.S. PATENT DOCUMENTS 6,476,208 B1 * 11/2002 Cohen et al. ................ 536/23.1

FOREIGN PATENT DOCUMENTS

| EP | 0931544 A2 | 7/1999 |
|----|------------|--------|
| JP | 64-090129 A | 6/1989 |
| JP | 11-158077 A | 6/1999 |
| JP | 2002-029980 A | 1/2002 |
| JP | 2003-113100 A | 4/2003 |
| KR | 2003-0079104 A | 10/2003 |
| KR | 10-2004-0026175 A | 3/2004 |
| WO | 2004/082700 A1 | 9/2004 |
| WO | 2005/021021 A1 | 3/2005 |

OTHER PUBLICATIONS

Xiong et al., "Effect of neferine on toxicodynamics of dichlorvos for inhibiting rabbit cholinesterase," Acta Pharmacol. Sin., vol. 24, No. 4, pp. 332-336, 2003.
Protais et al., "Effects of Various Isoquinoline Alkaloids On in Vitro $^3$H-Dopamine Uptake By Rat Striatal Synaptosomes," J. Nat. Prod., vol. 58, No. 10, pp. 1475-1484, 1995.
Yuji Watanabe, "Experimental Pharmacological Investigation of Isoquinoline-type Alkaloids on Psychotropic Activity," Suzuken Memorial Foundation, vol. 9, pp. 223-226, 1991. (English Translation in part).
Osamu Nishizaki, edited by Kenko Shokuhin no Tekisei Shiyo o Kangaeru Kai (Revised Edition), "Kenko Shokuhin Hyakka (Encyclopedia for Natural Ailment)", Buren Shuppan Kabushiki Kaisha Hakko, pp. 386-388, Mar. 25, 2003 (English translation in part).
Yasukawa et al., "Inhibitory Effect of Cepharanthine and its Related Compounds on 12-*O*- Tetradecanoylphorbol-13-Acetate-Induced Inflammation and Inhibition of Tumor Promotion by Cepharanthine in two-stage Carcinogenesis in Mice," Nihon Univ. J. Med., vol. 31, No. 4, pp. 229-234, 1989.
H. Tsukamoto et al, Alkaloids from embryo of the seed of *Nelumbo nucifera*, vol. 49 1986.
Vinod R. Hegde et al., "D4 Dopamine Receptor-Selective Compounds From The Chinese Plant Phoebe Chekiangensis", Bioorganic & Medicinal Chemistry Letters, vol. 7, No. 9, pp. 1207-1212, 1997.
Pulok K. Mukherjee et al., "Studies on psychopharmacological effects of *Nelumbo nucifera* Gaertn. rhizome extract", Journal of Ethnopharmacology, vol. 54, pp. 63-67, 1996.

(Continued)

*Primary Examiner*—Jennifer M Kim
(74) *Attorney, Agent, or Firm*—Browdy and Neimark, PLLC

(57) ABSTRACT

A method for preventing and/or alleviating a psychiatric disorder, and/or effectuating sedation, comprising administering a benzylisoquinoline derivative represented by General Formula (I):

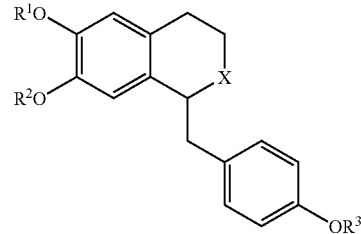

wherein $R^1$, $R^2$, $R^3$ and X each represent a particular group; a method for preventing and/or alleviating a particular symptom, comprising administering a bisbenzylisoquinoline derivative represented by General Formula (II):

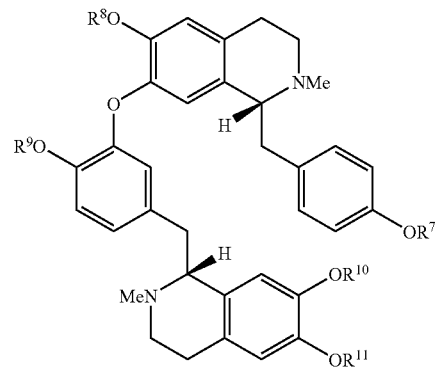

wherein $R^7$, $R^8$, $R^9$, $R^{10}$ and $R^{11}$ each represent a particular group, and a health food containing said derivative represented by General Formula (I) or (II).

3 Claims, No Drawings

OTHER PUBLICATIONS

Moonkyu Kang et al., "The anti-depressant effect of Nelumbinis semen on the rats under chronic mild stress inducing depression-like sympton", Database Biosis [Online] and FASEB Journal, vol. 18, No. 8, Suppl. S, pp. C209-210, May 2004. XP-002446733.

Andrew McDonald, "A botanical perspective on the identity of soma (*Nelumbo nucifera* gaertn.) based on scriptural and iconographic records", Database Biosis [Online] and Economic Botany, vol. 58, Suppl. S, pp. S147-S173, Jan. 2004. XP-002446734.

Xuemin Hu et al., "Studies on stability of liensinine injection", Database Biosis [Online] and China Journal of Chinese Materia Medica, vol. 18, No. 6, pp. 345-346 and 382, 1993. XP-002446735.

M. Kimura et al., "Anti-inflammatory effect of neolignans newly isolated from the crude drug 'Shin-i' (Flos magnoliae)", Database Embase [Online] and Plant Medica 1985 Germany, vol. 4, 291-293, 1985.

Supplementary European Search Report received Oct. 8, 2007.

Linde et al., "St John's wort for depression—an overview and meta-analysis of randomized clinical trials," British Medical Journal, vol. 313, Aug. 3, 1996, pp. 253-258.

"Comprehensive Dictionary of Chinese Medicines," Ed., Shanghai Science and Technology Publication and Shogakkan (1985), p. 2750.

Furukawa, Hiroshi, "On the Alkaloids of *Nelumbo nucifera* Gaertn. IX, Alkaloids of Loti Embryo. (2) Structure of Neferine, a New Biscoclaurine Alkaloid," Yakugaku Zasshi, 85(4),(1965), pp. 335-338.

Tomita et al., "On the Alkaloids of *Nelumbo nucifera* Gaertn. VIII. Studies on the Alkaloids of Loti Embryo. Structure of Isoliensinine, a New Biscoclaurine Type Alkaloid.," Chemical Pharmaceutical Bulletin, 13 (1965), pp. 39-41.

Kunitomo et al., "Alkaloids of *Nelumbo nucifera*," Phytochemistry, Pergamon Press, vol. 12 (1973), pp. 699-701.

Nishibe et al, "Alkaloids form Embryo of the Seed of *Nelumbo nucifera*," Journal of Natural Products, 49 (1986), p. 547.

Ito et al., Abstract of the $50^{th}$ Annual Meeting of the Japanese Society of Pharmacognosy, (2003), p. 116.

Nishibe, S., "Alkaloids from embryo of the seed of *Nelumbo nucifera*", Journal of Natural Products (1986) 49(3):548.

Wu, Shihua, "Preparative counter-current chromatography isolation of liensinine and its analogues from embryo of the seed of *Nelumbo nucifera* Gaertn, using upright coil planet centrifuge with four multiplayer coils connected in series", Journal of Chromatograohy A. (2004) 1041(1-2):153-162.

* cited by examiner

METHOD AND HEALTH FOOD FOR PREVENTING AND/OR ALLEVIATING PSYCHIATRIC DISORDER, AND/OR FOR EFFECTUATING SEDATION

BACKGROUND OF THE INVENTION

The present invention relates to a method for preventing and/or alleviating a psychiatric disorder, and/or effectuating sedation, comprising administering a benzylisoquinoline or bisbenzylisoquinoline derivative derived from lien tzehsin, and health food containing said derivative.

Psychiatric disorders are steadily increasing, reflecting the recent stressful society. The psychiatric disorders raise a serious social problem as the patients are inadaptable with society, and also an important issue from the viewpoint of medical economy. Drugs that are capable of affecting mental activity and behavior as the principal pharmacological action are called psychotropic drug, which are classified into integration ataxia drugs, mood-stabilizing drugs, antidepressants, antianxiety drugs, hypnotics, sedative drugs, antipsychotic drugs, antiepileptic drugs, alcohol deterrents, antiparkinson drugs, antidementia drugs, and the like. Various drugs with different action mechanisms have been developed and used for treatment of various psychiatric disorders.

For example, anxiety disorders, which are becoming more popular and an important social problem particularly recently, are generally classified into phobic anxiety disorder, agoraphobia, sociophobia, panic disorder, generalized anxiety disorder, obsessive compulsive disorder, certain phobia, and other anxiety disorders. These symptoms often appear in a complicated way.

The symptoms of depression include depressive condition, anhedonia, psychomotor retardation, thinking/cognitive dissonance, anxiety and impatience, autonomic nerve symptom, and the like.

Integration ataxia is a disease wherein integrating ability, an ability to integrate thinking, behavior, and emotion to fit for purpose, deteriorates gradually over an extended period of time and certain hallucination, delusion, and extremely unorganized behavior are observed during the deterioration process, but is rather indistinguishable from depression, maladjustment, or the like, and thus the final diagnosis thereof is made by the symptoms such as hallucination, delusion, and the like. However, the causes of the sickness are yet to be clearly understood, and the claim that integration ataxia is a single disease is still under a cloud.

Examples of the therapeutic drugs for the symptoms above are antidepressants currently used including tricyclic antidepressants such as imipramine, clomipramine, and trimipramine; tetracyclic antidepressants such as maprotiline and mianserin; triazolopyridine-based trazodone; benzketoxime-based selective serotonin reuptake inhibitor (SSRI) fluvoxamine; and the like.

Examples of the sleeping drugs include barbituric hypnotics used for quite a long time; benzodiazepine-based hypnotics such as triazolam, etizolam, brotizolamo, flunitrazepam, nitrazepam, quazepam, zopiclone and zolpidem which have been developed more recently; and the like. Further, favorable examples of the antianxiety drugs include the benzodiazepine-based drugs above, fluvoxamine and paroxetine, which are called SSRIs, and the like.

Drugs that have an action on the intracerebral dopamine nervous system have been used for treatment of integration ataxic, but also raised problems of extrapyramidal tract disorders (parkinsonian syndromes) as the adverse reactions, i.e., the adverse reactions observed as catalepsy in animal experiment systems. More recently, atypical antipsychotic drugs, which have an action also on the serotonin nervous system, were introduced and proven to be more effective in treating the disease. Other therapeutic drugs which have been used for treatment are called minor tranquilizers, which act on the cerebral limbic system in the brain such as thalamus, hippocampus, amygdala nidus, and the like and are said to alleviate selectively emotional disorders such as anxiety and stress and stabilize autonomic activities. Typical therapeutic drugs thereof are benzodiazepine compounds and azapyrone-based compounds. However, these drugs also carry the problem of side reactions such as motor coordination disorder, induction of catalepsy, and convulsive action induced by strychnine or picrotoxin.

However, it is pointed out that tricyclic or similar cyclic antidepressants cause anticholinergic actions such as dry mouth, eye adjustment disorder (misty vision), constipation, and dysuria, increase in body weight presumably caused by the antihistamic action, adrenolytic actions such as hypotension, dizziness, and stagger, adverse reactions such as cardiotoxic diseases, as well as acute poisoning by excessive intake.

It is also pointed out that the SSRI-group drugs may cause serotonin syndromes, although the adverse reactions thereof are significantly suppressed.

On the other hand, Saint John's Wort, for example, is famous as a health food for alleviating the various symptoms caused by the abnormality in the central nervous system, and said to be useful in the treatment of depression (Linde et al., British Medical Journal, 313 (1996) 253). Saint John's Wort, also called rose of Sharon, has long been used as a therapeutic drug for treatment of wound and neuralgia. Recently, it is widely used in the form of health food tablet mainly in Europe and North America as well as in Japan.

However, a component contained in Saint John's Wort is known to have a serious adverse reaction, photohypersensitivity, and another component a side reaction affecting the kinetics of cyclosporine metabolism in the body.

*Lotus* (Nelumbo nucifera Gaertner), a plant in water-lily family, has been widely used from root to flower as the ingredients for herbal cuisines from ancient days. In particular, lien tzehsin, green embryo of mature seed (Nelumbinis embryo), has been used in the oriental medicine for treatment of febrile diseases, care-laden vomiting of blood, and oneirogmus as it is said to have functions to reduce fevers, stop bleeding, slow ejaculation, and others ("Encyclopedia of Japanese and Chinese Medicines", Tsuneo Namba, p. 216 and "Comprehensive Dictionary of Chinese Medicines", Ed., Shanghai Science and Technology Publication and Shogakkan, (1985) p. 2750).

In studies on the active components mainly centered on the alkaloids of lien tzehsin, data on structural determination of the benzylisoquinoline and bisbenzylisoquinoline alkaloids were reported (Furukawa et al., Yakugaku Zasshi, 84 (1965) p. 335, Tomita et al., Chemical Pharmaceutical Bulletin, 13 (1965) p. 39 and Kunitomo et al., Phytochemistry, 12 (1973) p. 669), but no pharmacological effects of the alkaloids were reported except a kind of bisbenzylisoquinoline alkaloid, neferine.

On the other hand, with respect to recent studies on pharmacological effects of lien tzehsin, Nishibe et al. found the defervescent, antihypertensive, and antipsychotic actions thereof short time ago, but did not show any detailed grounds for the actions (Nishibe et al., Journal of Natural Products, 49 (1986) p. 547). Specifically, Nishibe et al. only disclosed (1) purification and isolation of four alkaloids from lien tzehsin, (2) animal tests concerning the antihypertensive activity, and (3) that one of the four alkaloids, neferine, exhibited an antihypertensive action, but there were no grounds for the defervescence and antipsychotic actions and no specific data concerning the antihypertensive activity (Nishibe et al., Journal of Natural Products, 49 (1986) p. 547).

In addition, the following two studies were reported at the meeting of the Pharmaceutical Society of Japan in 2002. Sato et al. reported from their rat studies that lien tzehsin had a thermoregulating function (Sato et al., Abstract of the 123rd annual meeting of the Pharmaceutical Society of Japan, No. 2, p. 112), while Kawashima et al. an anti-osteoporosis action of a lien tzehsin extract in the human osteoblast system (Kawashima et al., Abstract of the 123rd annual meeting of the Pharmaceutical Society of Japan No. 2, p. 146).

On the other hand, the inventors reported from mice studies that a component of lien tzehsin, neferine, exhibited a locomotor activity-inhibiting action (Ito et al., Abstract of the 50th annual meeting of the Japanese Society of Pharmocognosy, p. 116).

However, there are no known reports about the pharmacological effects of lien tzehsin components other than those described above.

An object of the present invention is to provide a method and a health food for preventing and/or alleviating a psychiatric disorder, and/or for effectuating sedation, in particular a method and a health food for preventing and/or alleviating at least one symptom selected from the group consisting of integration ataxia, depression, anxiety disorder, dysthymia, manic state, epilepsy, and sleep disorder, in which a natural product-derived substance safer even when taken for an extended period of term is used.

SUMMARY OF THE INVENTION

As a result of extensive investigation for a safer substance acting on the central nervous system for the purpose above, the inventors have found a substance higher in safety and neurotropic action among the benzylisoquinoline and bisbenzylisoquinoline derivatives extracted from lien tzehsin and thus achieved the present invention.

Accordingly, the present invention relates to a method for preventing and/or alleviating a psychiatric disorder, and/or for effectuating sedation, comprising administering to a patient in need thereof, as an active ingredient, at least one benzylisoquinoline derivative represented by General Formula (I):

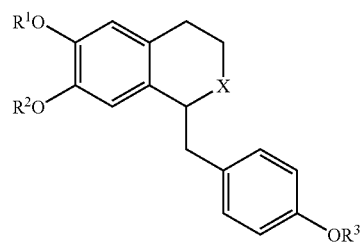

wherein $R^1$, $R^2$ and $R^3$ each independently represent a hydrogen atom, a $C_{1-6}$ alkyl group which may be substituted, an aryl group which may be substituted or a heteroaryl group which may be substituted; and X represents $NR^4$ or $N^+R^5R^6Y$ in which $R^4$ represents a hydrogen atom or a $C_{1-6}$ alkyl group; $R^5$ and $R^6$ each independently represent a hydrogen atom or a $C_{1-6}$ alkyl group; and Y represents a halide, hydroxide, or sulfate ion, or a pharmaceutically allowable salt thereof.

In the above method for alleviating a psychiatric disorder, the patient in need thereof is preferably one having at least one symptom selected from the group consisting of integration ataxia, depression, anxiety disorder, dysthymia, manic state, epilepsy, and sleep disorder.

In the above method for effectuating sedation, the patient in need thereof is preferably a patient in need of sedation.

The present invention is also related to a method for preventing and/or alleviating a symptom selected from the group consisting of integration ataxia, depression, anxiety disorder, dysthymia, manic state, epilepsy, and sleep disorder, comprising administering to a patient in need thereof, as an active ingredient, at least one bisbenzylisoquinoline derivative represented by General Formula (II):

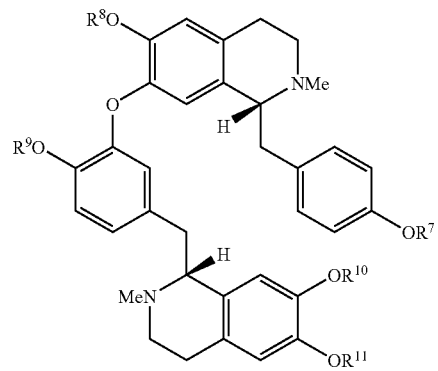

wherein $R^7$, $R^8$, $R^9$, $R^{10}$ and $R^{11}$ each independently represent a hydrogen atom, a $C_{1-6}$ alkyl group which may be substituted, an aryl group which may be substituted or a heteroaryl group which may be substituted, or a pharmaceutically allowable salt thereof.

In the present invention, the derivative represented by General Formula (II) is preferably neferine:

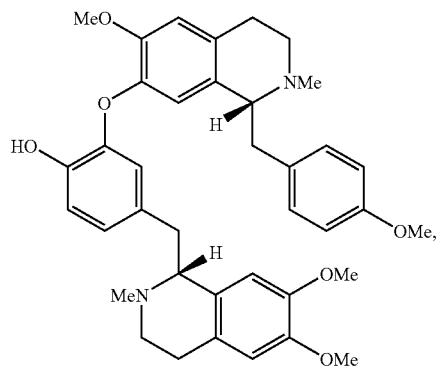

liensinine:

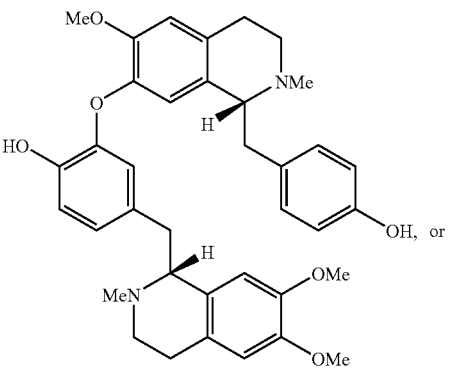

OH, or isoliensinine:

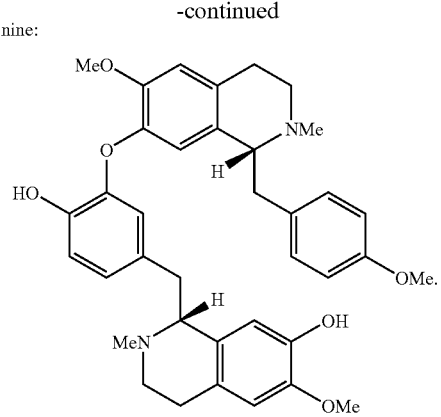

The present invention relates to a method for bringing about a psychotropic action, comprising administering to a patient in need thereof, as an active ingredient, at least one benzylisoquinoline derivative represented by General Formula (I):

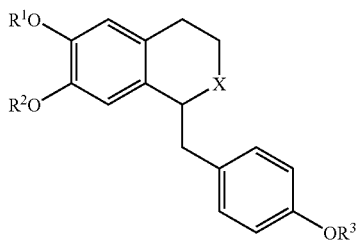

wherein $R^1$, $R^2$ and $R^3$ each independently represents a hydrogen atom, a $C_{1-6}$ alkyl group which may be substituted, an aryl group which may be substituted or a heteroaryl group which may be substituted; and X represents $NR^4$ or $N^+R^5R^6Y$ in which $R^4$ represents a hydrogen atom or a $C_{1-6}$ alkyl group; $R^5$ and $R^6$ each independently represent a hydrogen atom or a $C_{1-6}$ alkyl group; and Y represents a halide, hydroxide, or sulfate ion, or a pharmaceutically allowable salt thereof.

In the method for bringing about a psychotropic action, preferably, the psychotropic action is a sedation and the patient in need is one in need of sedation.

In the method for bringing about a psychotropic action, preferably, the psychotropic action is the alleviation of psychiatric disorder and the patient in need is one having at least one symptom selected from the group consisting of integration ataxia, depression, anxiety disorder, dysthymia, manic state, epilepsy, and sleep disorder.

In the present invention, the derivative represented by General Formula (I) or (II) is preferably administered orally as part of a health food.

The present invention is also related to a neurotropic health food containing a compound represented by the General Formula (I).

The present invention is also related to a health food for preventing and/or alleviating a symptom selected from the group consisting of integration ataxia, depression, anxiety disorder, dysthymia, manic state, epilepsy, and sleep disorder, containing a compound represented by the General Formula (II).

The health food is preferably a beverage or drinkable preparation.

DETAILED DESCRIPTION

The benzylisoquinoline derivative according to the present invention is a compound represented by General Formula (I):

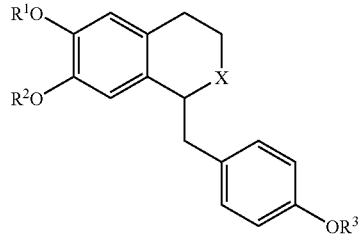

wherein $R^1$, $R^2$ and $R^3$ each independently represent a hydrogen atom, a $C_{1-6}$ alkyl group which may be substituted, an aryl group which may be substituted or a heteroaryl group which may be substituted; and X represents $NR^4$ or $N^+R^5R^6Y$ in which $R^4$ represents a hydrogen atom or a $C_{1-6}$ alkyl group; $R^5$ and $R^6$ each independently represent a hydrogen atom or a $C_{1-6}$ alkyl group; and Y represents a halide, hydroxide, or sulfate ion.

The bisbenzylisoquinoline derivative according to the present invention is a compound represented by General Formula (II):

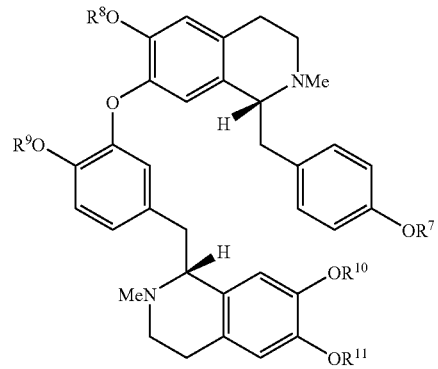

wherein $R^7$, $R^8$, $R^9$, $R^{10}$ and $R^{11}$ each independently represent a hydrogen atom, a $C_{1-6}$ alkyl group which may be substituted, an aryl group which may be substituted or a heteroaryl group which may be substituted.

In the compounds represented by General Formula (I) or (II) above, the $C_{1-6}$ alkyl group in "a $C_{1-6}$ alkyl group which may be substituted" is, for example, a straight-chain or branched-chain alkyl group having 1 to 6 carbons such as a methyl, ethyl, propyl, isopropyl, n-butyl, t-butyl, pentyl, hexyl, or other group. The substituents for these $C_{1-6}$ alkyl group include for example halogen atoms. The "$C_{1-6}$ alkyl group which may be substituted" is preferably a methyl group, from the viewpoints of its presence in natural lien tzehsin in a greater amount and the long dietary habits.

In the compounds represented by General Formula (I) or (II) above, the aryl group in "an aryl group which may be substituted" favorably used is a phenyl, naphthyl, anthryl, or other group. The substituents for these aryl groups include, for example, halogen atoms, $C_{1-6}$ alkyl groups and the like, and examples of the substituted aryl groups include toluyl, phenethyl, and other groups.

Examples of the heteroaryl groups favorably used in "a heteroaryl group which may be substituted" include furyl, thiophenyl, pyrrolyl, thiazolyl, isothiazolyl, oxazolyl, isooxazolyl, imidazolyl, triazolyl, pyridyl, pyrimidyl, pyrazonyl, quinolyl, benzothiophenyl, and morpholyl groups, and the like. The substituents for these heteroaryl groups include, for example, halogen atoms, $C_{1-6}$ alkyl groups, and the like.

Typical examples of the benzylisoquinoline derivative according to the present invention include, but are not particularly limited to:

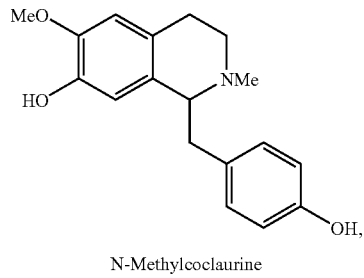

N-Methylcoclaurine

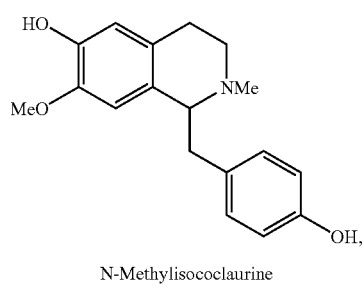

N-Methylisococlaurine

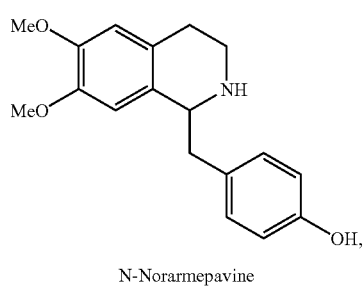

N-Norarmepavine

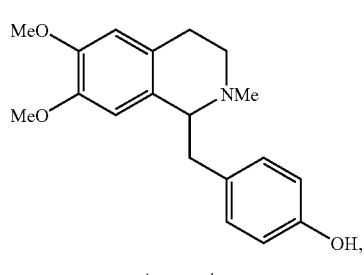

Armepavine

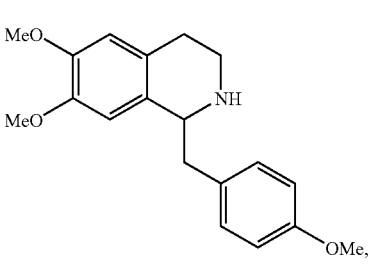

O, O-Dimethylcoclaurine,

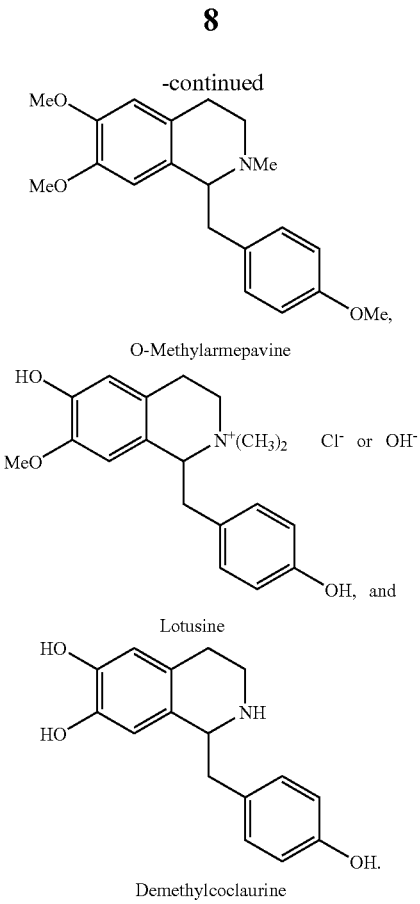

O-Methylarmepavine

Lotusine

Demethylcoclaurine

Typical examples of the bisbenzylisoquinoline derivatives according to the present invention include, but are not particularly limited to:

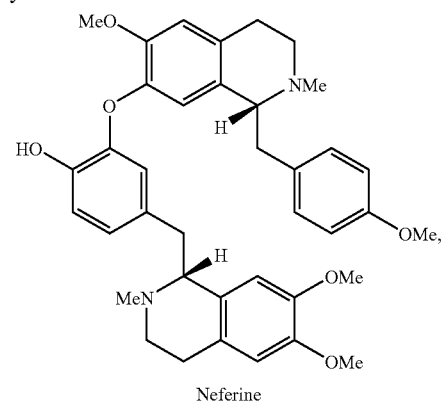

Neferine

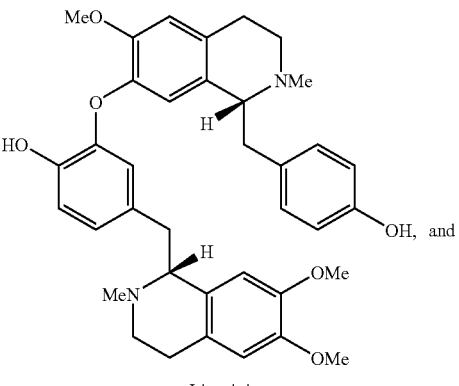

Liensinine

-continued

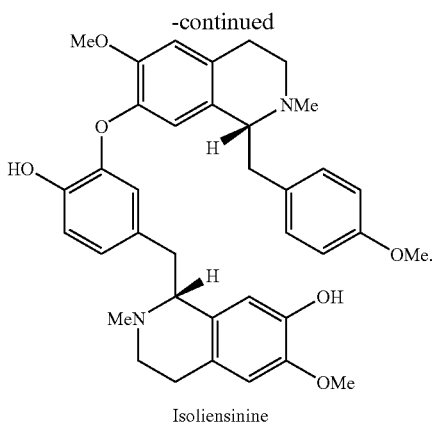

Isoliensinine

Further, the salt of the compound represented by Formula (I) or (II) is any one of the pharmaceutically allowable salts thereof. The pharmaceutically allowable salt is any one of the salts with inorganic and organic bases and inorganic and organic acids, and typical examples thereof include salts such as hydrochloride, gluconate, p-toluenesulfonate, fumarate, citrate, succinate, salicylate, oxalate, lactate, hydrobromide, phosphate, methanesulfonate, benzenesulfonate, pamoate, benzoate, tartrate, nitrate, maleate, di-p-toluoyltartrate, acetate, sulfate, hydroiodide, mandelate, and the like.

The compounds represented by Formulae (I) and (II) used in the present invention can be prepared according to the method same as or similar to those described in T. Kametani, S. Takano, J. Chem. Soc. (C), 1969, 298-300 and T. Kametani, H. Yagi, S. Kaneda, Chem. Pharm. Bull. 14 (9), 947-980, (1966).

For example, the compounds represented by Formula (I) can be prepared by reacting phenethylamine and phenylacetic acid respectively having a corresponding substituent into an amide, and cyclizing the amide with phosphorus oxychloride or the like into an isoquinoline skeleton. In addition, a substituent may be introduced on the amine in the isoquinoline skeleton if needed according to any one of the known methods.

The compound represented by Formula (II) can be prepared, for example, by condensing two molecules of a derivative having an isoquinoline skeleton, i.e., a compound represented by Formula (I), in a coupling reaction such as copper-catalyzed Ullmann reaction or the like into a compound represented by Formula (II) having a bisisoquinoline skeleton.

Alternatively, the compound represented by Formula (I) or (II) used in the present invention is an extract of lien tzehsin prepared by a conventional extraction technique from natural products.

In the present invention, the compounds represented by Formula (I) may be used alone or in combination of two or more compounds and the compounds represented by Formula (II) may also be used alone or in combination of two or more compounds. Further, the compound represented by Formula (I) and the compound represented by Formula (II) may be used in combination.

If the compound is to be isolated by extraction, lien tzehsin is, for example, dried and then extracted with an organic solvent such as methanol, ethanol, aqueous ethanol, hexane or chloroform under heat, and the extract is concentrated. The compound may be purified and isolated by applying the extract thus obtained onto an absorbent such as silica gel and eluting with a chloroform/methanol mixture as the eluent. The extraction fraction containing the compound represented by Formula (I) or (II) according to the present invention may be used as it is as a mixture without further purification as the benzylisoquinoline or dibenzylisoquinoline derivative according to the present invention.

In this manner, compounds prepared by synthesis or extracted and isolated from lien tzehsin may be used as the compound represented by Formula (I) or (II) according to the present invention.

In addition, the compound represented by Formula (I) or (II) may be used as an active ingredient in the present invention, or alternatively, a lien tzehsin extract containing the compounds may also be used as the active ingredient.

Lien tzehsin containing these benzylisoquinoline and bisbenzylisoquinoline derivatives has been taken for a long time as described above and thus proven to be a safe food. Lien tzehsin is available from many Chinese herbal medicine shops, for example, from Shanghai Traditional Chinese Medical Co., Ltd. (110 Yan An Road, Shanghai, China) or others.

Methods of administering the psychotropic drug according to the present invention are not particularly limited and include oral, intravenous, intramuscular, subcutaneous, percutaneous, transmucosal, intraperitoneal, and other administrations, and oral administration is preferably as it is more convenient for the people who intake.

A variety of dosage forms are possible as the dosage form of the psychotropic drug according to the present invention, but a dosage form allowing oral administration is preferably. Examples of the dosage forms include, but are not limited to, tablet, capsule, powder, granule, solution, spirit, syrup, and the like. In addition, various pharmaceutically allowable additives may be added to the formulation, and examples thereof include, but are not limited to, excipient, flavor, colorant, sweetener, emulsifier, coating agent, vitamin C, antioxidant, and the like.

The dosage of the psychotropic drug according to the present invention for an adult is 0.1 to 200 mg, preferably 0.1 to 100 mg per day in the case of a benzylisoquinoline derivative, and 1 to 2,000 mg, preferably 1 to 1,000 mg in the case of a bisbenzylisoquinoline derivative. Needless to say, the dosage may be altered according to the age, body weight, symptom, administration method, and the like of the individual who is administered.

The drug may be divided and administered several times a day. In addition, the drug may be administered in combination with another antidepressant or therapy.

The psychotropic drug containing the benzylisoquinoline derivative according to the present invention is effective in preventing and/or alleviating the symptoms selected from the group consisting of integration ataxia, depression, anxiety disorder, dysthymia, manic state, epilepsy and sleep disorder, and has a sedative action.

Another embodiment of the present invention is a health food containing the compound represented by Formula (I) or (II).

In the present invention, the term "health foods" is a commonly used term meaning the foods sold by claiming that the food is better for health than common foods. Currently in Japan, there is no particular law governing the so-called health foods, which are mainly regulated by the Food Sanitation Law, the Nutrition Improvement Law, and the Pharmaceutical Affairs Law. In April 2001, a new functional health food system was established, and in addition to the conventional foods for specified health use (specified health foods), a new class of "foods with nutrient functional claims" that allows claims of the nutritional functions of part of vitamins and minerals is ordained. The health foods according to the invention include all of these foods. The "health foods" according to the present invention include "special-purpose foods" for use in specific health use, i.e., nutritional supplement foods which are defined generally as "the foods sold for nutrient supplementation or specific health use, in the form different from ordinary foods such as tablet, capsule, and the like".

The health food according to the present invention may be in any form of, for example, tablet, capsule, powder, granule, solution, spirit, syrup, or the like, if it can be taken orally. In addition, the compound represented by Formula (I) or (II) may be processed into various foods and drinks by using it as the raw material. Examples of such foods and drinks include noodle, porridge, risotto, jelly, cookie, soup, and beverage, but are not limited thereto.

In addition, various pharmaceutically allowable additives such as excipient, flavor, colorant, sweetener, emulsifier, coating agent, vitamin C, and antioxidant; minerals such as iron, magnesium, and calcium; vitamins; dietary fibers such as alginic acid; as well as various proteins, lipids, saccharides such as lactose and the like may be added to these foods.

Further, health foods having an action to alleviate the symptoms above triggered by mental stress or the like can be prepared by using American ginseng extract, *ginkgo biloba* extract, soybean extract, licorice extract, pomegranate extract, yam extract or the like in combination with the health food according to the present invention.

Drinkable preparations are prepared by blending the compound represented by Formula (I) or (II) and water as the primary ingredients. The ratio of the compound represented by Formula (I) or (II) to water in the mixture is not particularly limited but is suitably in the range of 1:5,000 to 1:100,0000 by weight, preferably 1:10,000 to 1:100,000.

Health food tablets containing the compound represented by Formula (I) or (II) can be prepared by adding a diluent and various additives such as creamy powder, malt sugar, cellulose powder, sugar ester, potassium phosphate, starch glycolic acid sodium, calcined calcium, oyster shell powder, cyclodextrin, magnesium citrate, and the like and tabletting the resulting mixture directly by powder compression method.

The dosage of the health food or beverage according to the present invention is not particularly limited, and may be altered arbitrarily according to the administration form, age, body weight, and symptoms.

Actions of the compound represented by Formula (I) or (II) according to the present invention on the central nervous system can be evaluated by the screening tests commonly practiced in the art, i.e., animal testing methods used for evaluation of various actions and pharmacological effects in the field of neurotropic action. For example, sedative action can be evaluated by locomotor activity suppression test [Hirose, A., Kato, T., Shimizu, H., Tanaka, H., Nakamura, N., Katsube, J., Jpn. J. Pharmacol. 53, 321-329 (1990)]; therapeutic action on integration ataxia, methamphetamine-induced locomotor activity suppression test [Hirose, A., Kato, T., Shimizu, H., Tanaka, H., Nakamura, N., Katsube, J., Jpn. J. Pharmacol. 53, 321-329 (1990)]; antidepressive action, forced swimming test [Porsolt, R. D., Bertin, A., Jalfre, M., Arch. Int. Pharmacodyn. 299, 327-336 (1977)]; antianxiety action, elevated plus-maze test [Lister, R. G., Psychopharmacology, 112, 13-20 (1993)]; the therapeutic action on obsessive compulsive disorders, glass ball-covering behavior test [Njung'e, K., Hadley, S. L., Pharmacol. Biochem. Behav., 38, 65-67 (1991)]; sleep disorder improvement action, thiopental sleep enhancing test [Sukma, M., Chaichamtipyuth, C., Murakami, Y., Tohda, M., Matsumoto, K., Watanabe, H., J. Ethopharmacology, 83, 87-94 (2002)].

In addition, adverse reactions often associated with conventional drugs such as decline of motor coordination and catalepsy induction can be evaluated by animal testing methods such as rotarod test [Souri, E., Sharifzadeh, M., Farasam, H., Gharavi, N., J. Pharm. Pharmacol, 51, 853-855 (1999)] and catalepsy test [Hirose, A., Kato, T., Shimizu, H., Tanaka, H., Nakamura, N., Katsube, J., Jpn. J. Pharmacol. 53, 321-329 (1990)].

Hereinafter, the present invention will be described in more detail with reference to the following Preparative Examples and Examples, but it should be understood that the present invention is not particularly limited thereto. Various modifications to the benzylisoquinoline and bisbenzylisoquinoline derivatives according to the invention are possible by persons skilled in the art, but these modifications are also embraced by the present invention.

PREPARATIVE EXAMPLE 1

(Extraction of Bisbenzylisoquinoline Derivatives)

Lien tzehsin (Shanghai Traditional Chinese Medical Co., Ltd., 110 Yan An Road, Shanghai, China) was first washed thoroughly with water and then dried. 500 g of the dried lien tzehsin was extracted three times with 1 L of ethanol while heated under reflux. The extract thus obtained was filtered and dried under reduced pressure, to give approximately 50 g of paste. Quantitative determination of the bisbenzylisoquinoline derivatives by using the Rf values obtained by thin layer chromatography of the paste obtained (silica gel 60F254, chloroform/methanol/ammonia water: 90/9/1) revealed that the contents of neferine, liensinine, isoliensinine, and thalifoline were respectively 0.4%, 0.1%, 0.1%, and 0.1%. The extract was used in the following Examples as Extract 1.

PREPARATIVE EXAMPLE 2

(Extraction of Bisbenzylisoquinoline Derivatives)

Lien tzehsin was first washed thoroughly with water and then dried. 1,200 g of the dried lien tzehsin was extracted three times with 2 L of hot methanol. The methanol extract thus obtained was evaporated to dryness under reduced pressure, resuspended in water, and extracted with n-hexane and chloroform sequentially. The chloroform-soluble fraction was evaporated to dryness under reduced pressure, to give a solid matter in an amount of approximately 8 g. Then, the solid matter was further purified by the methods described below.

Namely, the solid matter was purified by using a column of 580 mm in length and 46 mm in diameter containing 160 g of silica gel as a packing material. It was fractionated by using a gradient mixed chloroform/methanol solution as the eluent. Solid matter in an amount equivalent to 489 mg was obtained as the 20% methanol fraction. Quantitative determination of the bisbenzylisoquinoline derivatives by using the Rf values obtained by thin layer chromatography of the paste obtained (silica gel 60F254, chloroform/methanol/ammonia water: 90/9/1) revealed that the contents of neferine, liensinine, and isoliensinine were respectively 4.0%, 7.0%, and 1.8%. The solid matter was used as Extract 2 in the following Examples.

PREPARATIVE EXAMPLE 3

(Isolation of Neferine)

Lien tzehsin was first washed thoroughly with water and then dried. 1,200 g of the dried lien tzehsin was extracted three times with 2 L of hot methanol. The methanol extract thus obtained was evaporated to dryness under reduced pressure, resuspended in water, and extracted with n-hexane and chloroform sequentially. The chloroform-soluble fraction was evaporated to dryness under reduced pressure, to give of solid matter in an amount of approximately 8 g. Then, the solid matter was further purified by the methods described below.

Namely, the solid matter was purified by using a column of 580 mm in length and 46 mm in diameter containing 160 g of silica gel as a packing material. It was fractionated by using a gradient mixed chloroform/methanol solution as the eluent. Solid matter in an amount equivalent to 2.16 g was obtained as the 5% methanol fraction.

The crystalline solid thus obtained had a TLC Rf value of 0.39 (silica gel 60F254, chloroform:methanol:ammonia water: 90:9:1). Hydrogen signals corresponding to two N-methyl and three methoxyl groups and 11 aromatic hydrogen signals were observed in $^1$H-NMR, and together with the results of MS, UV, and IR analysis, the compound was identified as neferine. Analytical values of the neferine are shown below:

$^1$H-NMR (CDCl$_3$): [δ 2.49, 2.52 (6H, each s)], [δ 3.51, 3.73, 3.80, 3.81 (12H, each s)], [δ 5.96 (1H, s), 6.35 (1H, s), 6.51 (1H, s), 6.54 (1H, d, J=2.0 Hz), 6.64 (1H, s), 6.69 (2H, d, J=8.5 Hz), 6.70 (1H, dd, J=8.0, 2.0 Hz), 6.86 (1H, d, J=8.0 Hz), and 6.90 (2H, d, J=8.5 Hz)].

EI-MS m/z: 624 [M]$^+$, 503, and 206.

UV λmax (MeOH) nm (log ε): 230 sh (4.47), and 283 (4.00).

IR νmax (KBr) cm$^{-1}$: 3421, 1612, and 1510.

PREPARATIVE EXAMPLE 4

(Isolation of Liensinine and Isoliensinine)

In a similar manner to Preparative Example 3, lien tzehsin was first washed thoroughly with water and then dried. 1,200 g of the dried lien tzehsin was extracted three times with 2 L of hot methanol. The methanol extract thus obtained is evaporated to dryness under reduced pressure, resuspended in water, and extracted with n-hexane and chloroform sequentially. The chloroform-soluble fraction was evaporated to dryness under reduced pressure, to give of solid matter in an amount of approximately 8 g. The solid matter was purified by using a column of 580 mm in length and 46 mm in diameter containing 160 g of silica gel as a packing material. It was fractionated by using a gradient mixed chloroform/methanol solution as the eluent. The 20% methanol elution fraction (488.5 mg) was further subjected to a silica gel chromatography and eluted with a chloroform-methanol. The resulting 7.5% methanol elution fraction (16.4 mg), 10% methanol elution fraction (40.8 mg), 15% methanol elution fraction (74.9 mg) 20% methanol elution fraction (33.0 mg), and 30% methanol elution fraction (82.8 mg) were subjected respectively to a preparative thin layer chromatography (developing solvent, chloroform:methanol:ammonium hydroxide: 90:9:1), to isolate neferine (19.7 mg), crude liensinine (41.3 mg), and crude isoliensinine (12.5 mg). These crude compounds were further purified with another similar preparative thin layer chromatography respectively, to give liensinine (34.1 mg) and isoliensinine (8.9 mg). Analytical values thereof are shown respectively below:

Liensinine $^1$H-NMR (CDCl$_3$): [δ 2.55, 2.59 (6H, each s)], [δ 3.43, 3.84, 3.90 (9H, each s)], [δ 5.71 (1H, s), 6.39 (1H, dd, J=8.0, 2.0 Hz), 6.44 (1H, s), 6.59 (1H, s), 6.69 (1H, s), 6.72 (1H, d, J=8.0 Hz), 6.81 (2H, d, J=8.5 Hz), 6.81 (1H, d, J=2.0 Hz), and 7.00 (2H, d, J=8.5 Hz].

SI-MS m/z: 611 [M+H]$^+$, 503, and 206.

UV λmax (MeOH) nm (log ε): 228 sh (4.43), and 282 (3.96).

IR νmax (KBr) cm$^{-1}$: 3415, 1612, and 1514.

Isoliensinine $^1$H-NMR (CDCl$_3$): [δ 2.39, 2.51 (6H, each s)], [δ 3.74, 3.80, 3.81 (9H, each s), (δ 6.32 (1H, s), 6.37 (1H, s), 6.46 (1H, s), 6.49 (1H, d, J=2.0 Hz), 6.65 (1H, s), 6.71 (2H, d, J=8.5 Hz), 6.73 (1H, dd, J=8.0, 2.0 Hz), 6.83 (1H, d, J=8.0 Hz), and 6.91 (2H, d, J=8.5 Hz)].

CI-MS m/z: 611 [M+H]$^+$.

UV λmax (MeOH) nm (log ε): 230 sh (4.44) and 283 (4.02).

IR νmax (KBr) cm$^{-1}$: 3394, 1611, and 1514.

PREPARATIVE EXAMPLE 5

(Synthesis of N-norarmepavine)

4.02 g (22.2 mmol) of 3,4-Dimethoxyphenethylamine and 3.37 g (22.2 mmol) of p-hydroxyphenylacetic acid were stirred under argon airflow at 170° C. for an hour and 15 minutes. Methanol was added to the cooled reaction solution and the resulting crystals were collected by filtration, to give an amide in an amount of 4.29 g. Into a solution of the amide 4.02 g (12.8 mmol) in 80 mL of acetonitrile, 8.0 mL of phosphorus oxychloride was added dropwise at room temperature, and the mixture was then heated under reflux on an oil bath for 15 minutes. After cooled, the mixture was evaporated under reduce pressure, and the resulting residue was redissolved in 80 mL of methanol. After adjustment of the pH of the mixture to pH 7 to 8 by addition of ammonia water, 800 mg of NaBH$_4$ was added gradually and the mixture was stirred at room temperature for 30 minutes. After evaporation of the solvent under reduced pressure, the resulting alkaloid was extracted with chloroform and purified by column chromatography, to give 2.46 g of N-norarmepavine (yield 64%). Analytical values thereof are shown below:

mp: 199-201° C. (MeOH, hydrochloride). EI-MS m/z: 296 and 192 (100%).

CI-MS m/z: 300 [M+H]$^+$. $^1$H-NMR: δ (CDCl$_3$, 200 MHz) 2.76 (2H, brt, J=6.0 Hz, H2-4), 2.86 (1H, dd, J=14.0, 9.0 Hz, H-α), 2.95 (1H, dt, J=12.5, 6.0 Hz, H-3), 3.15 (1H, dd, J=14.0, 4.0 Hz, H-α), 3.24 (1H, dt, J=12.5, 6.0 Hz, H-3), 3.84, 3.86 (6H, each s, OMe x 2), 4.15 (1H, dd, J=9.0, 4.0 Hz, H-1), 6.59, 6.66 (2H, each s, H-5, 8), 6.65 (2H, d, J=8.5 Hz, H-11, 13), and 7.03 (2H, d, J=8.5 Hz, H-10, 14).

PREPARATIVE EXAMPLE 6

(Synthesis of Armepavine)

1.20 g (4.01 mmol) of N-norarmepavine obtained in Preparative Example 5 was dissolved in 45 mL of methanol. After addition of 2.22 mL of formalin, the mixture was stirred at room temperature for 30 minutes, added with 890 mg of NaBH$_4$, and stirred additionally at room temperature for 30 minutes. After evaporation of the solvent under reduced pressure, the resulting alkaloid was extracted with chloroform and purified by column chromatography, to give 1.12 g of armepavine (yield 89%). Analytical values are shown below:

EI-MS: m/z 311 and 206 (100%). CI-MS m/z: 314 [M+H]$^+$. $^1$H-NMR: δ (CDCl$_3$, 300 MHz) 2.52 (3H, s, NMe), 2.62 (1H, m, H-4), 2.74 (1H, dd, J=13.5, 8.0 Hz, H-α), 2.78-2.95 (2H, m, H-3, 4), 3.14 (1H, dd, J=13.5, 5.0 Hz, H-α), 3.26 (1H, m, H-3), 3.54 (3H, s, OMe), 3.72 (1H, dd, J=8.0, 5.0 Hz, H-1), 3.83 (3H, s, OMe), 5.99, 6.56 (2H, each s, H-5, 8), 6.63 (2H, d, J=8.5 Hz, H-1, 13), and 6.90 (2H, d, J=8.5 Hz, H-10, 14).

PREPARATIVE EXAMPLE 7

(Synthesis of O,O-dimethylcoclaurine)

8.01 g (44.3 mmol) of 3,4-dimethoxyphenethylamine and 7.34 g (44.2 mmol) of p-methoxyphenylacetic acid were stirred under argon airflow at 170° C. for an hour and 30 minutes. Methanol was added to the cooled reaction solution and the resulting crystals are collected by filtration, to give 12.5 g of an amide (yield 86%). 5.00 g (15.2 mmol) of the amide was dissolved in 100 mL of acetonitrile, and 10.0 mL of phosphorus oxychloride was added dropwise to the mixture at room temperature, and the mixture was heated under reflux on an oil bath for additionally 30 minutes. After the solvent was removed by distillation under reduced pressure. The residue was redissolved in 100 mL of methanol. After adjustment of the solution to pH 7 to 8 by addition of ammonia water, 1.52 g of NaBH$_4$ was added gradually and the mixture was stirred at room temperature for 15 minutes. After removal of the solvent by distillation under reduced pressure, the resulting alkaloid was extracted with chloroform and purified by column chromatography, to give 4.43 g of O,O-dimethylcoclaurine (yield 93%).

Analytical values are shown below:

mp: 185-187° C. (MeOH, hydrochloride). EI-MS m/z: 313 [M]$^+$ and 192 (100%). CI-MS: m/z 314 [M+H]$^+$. $^1$H-NMR: δ (CDCl$_3$, 300 MHz) 2.69 (1H, dt, J=16.0, 6.0 Hz, H-4), 2.77 (1H, brdt, J=16.0, 6.0 Hz, H-4), 2.87 (1H, dd, J=14.0, 9.0 Hz, H-α), 2.92 (1H, dt, J=12.0, 6.0 Hz, H-3), 3.15 (1H, dd, J=14.0, 4.5 Hz, H-α), 3.21 (1H, dt, J=12.0, 6.0 Hz, H-3), 3.80, 3.81, 3.86 (9H, each s, OMe x 3), 4.11 (1H, dd, J=9.0, 4.5 Hz, H-1), 6.59, 6.62 (2H, each s, H-5, 8), 6.87 (2H, d, J=8.5 Hz, H-11, 13), and 7.17 (2H, d, J=8.5 Hz, H-10, 14).

PREPARATIVE EXAMPLE 8

(Synthesis of O-methylarmepavine)

1.51 g (4.82 mmol) of O,O-dimethylcoclaurine obtained in Preparative Example 7 was dissolved in 75 mL of methanol and added with 3.0 mL of formalin, and the mixture was stirred at room temperature for 30 minutes. After addition of 1.21 g of NaBH$_4$, the mixture was further stirred at room temperature for 30 minutes. After evaporation of the solvent under reduced pressure, the alkaloid was extracted with chloroform and purified by column chromatography, to give 1.19 g of O-methylarmepavine (yield 75%). Analytical values are shown below:

EI-MS: m/z 326 and 206 (100%). CI-MS: m/z 328 [M+H]$^+$. $^1$H-NMR: δ (CDCl$_3$, 300 MHz) 2.53 (3H, s, NMe), 2.59 (1H, m, H-4), 2.75 (1H, dd, J=13.0, 7.5 Hz, H-α), 2.74-2.89 (2H, m, H-3, 4), 3.14 (1H, dd, J=13.0, 5.0 Hz, H-α), 3.18 (1H, m, H-3), 3.55, 3.77, 3.83 (9H, each s, OMe x 3), 3.67 (1H, dd, J=7.5, 5.0 Hz, H-1), 6.01, 6.55 (2H, each s, H-5, 8), 6.80 (2H, d, J=8.5 Hz, H-11, 13), and 7.01 (2H, d, J=8.5 Hz, H-10, 14).

In the following Examples, all extracts and drugs used were dissolved in physiological saline before use for i.p. administration and the dose was 0.1 ml of physiological saline per 10 g of mouse body weight in either case. All extracts and drugs were suspended in physiological saline containing 1% carboxymethylcellulose before use for oral administration and the dose was 0.1 ml of 1% carboxymethylcellulose-containing physiological saline suspension per 10 g of mouse body weight in either case. Male ICR mice (Japan SLC) having a body weight of 25 to 30 g were used in the tests below unless otherwise stated, and were fed in advance at a room temperature of 23±1° C. and a relative humidity of 55±5% in the environment of a 12-hour-light and 12-hour-dark cycle at 7 and 19 for 3 to 5 days. The mice were allowed to have water and feed freely.

EXAMPLE 1

(Evaluation of Sedative Action)

Twenty five mice were grouped into five groups each having five mice, to which 5 mg/kg of N-methylcoclaurine hydrochloride (treatment group 1-1: i.p. administration), 50 mg/kg of neferine hydrochloride (treatment group 1-2: oral administration, and treatment group 1-3: i.p. administration), 50 mg/kg of liensinine hydrochloride (treatment group 1-4: oral administration), or physiological saline (negativity control group 1-1: i.p. administration) was administered. The ultromotivity of the mice was analyzed by using a locomotor activity monitoring system (NS-AS01, Neuroscience Inc.). The ultromotivity measurements were performed at an interval of 5 minutes for 60 minutes, and the ultromotivity was judged from the count at each measuring time. The results are summarized in TABLE 1.

TABLE 1

| Test group | Ultromotivity (count) | |
|---|---|---|
| | 30 minutes | 60 minutes |
| Treatment group 1-1 (N-methylcoclaurine, i.p.) | 250 | 250 |
| Treatment group 1-2 (neferine, oral) | 500 | 750 |
| Treatment group 1-3 (neferine, i.p.) | 500 | 760 |
| Treatment group 1-4 (liensinine, oral) | 600 | 800 |
| Negative control group 1-1 (physiological saline, i.p.) | 900 | 1250 |

The results above indicated that the compounds used in treatment groups exerted an obvious sedative action both in oral and i.p. administration. The results also indicated that a benzylisoquinoline derivative, N-methylcoclaurine, had an extremely higher activity than bisbenzylisoquinoline derivatives, neferine and liensinine.

Similar tests were conducted by i.p. administration of 25 mg/kg of N-norarmepavine (treatment group 1-5, n=6), 25 mg/kg of O,O-dimethylcoclaurine (treatment group 1-6, n=5), 10 mg and 25 mg/kg of armepavine (respectively, treatment group 1-7, n=6, and treatment group 1-8, n=6), 10 mg and 25 mg/kg of O-methylarmepavine (respectively, treatment group 1-9, n=6, and treatment group 1-10, n=6), and physiological saline (negativity control group 1-2, n=5). The ultromotivity measurements were performed at an interval of five minutes for 60 minutes, and the ultromotivity was subjected to a significant difference test (Tukey's method) by using the counts at respective measuring times. The results are summarized in TABLE 2.

TABLE 2

| Test group | Ultromotivity (count) | |
|---|---|---|
| | 30 minutes | 60 minutes |
| Treatment group 1-5 (N-norarmepavine) | 792.0* ± 71.8 | 1049** ± 85.5 |
| Treatment group 1-6 (O,O-dimethylcoclaurine) | 723.4* ± 68.6 | 1091** ± 188.8 |
| Treatment group 1-7 (armepavine) | 699.3** ± 126.6 | 1107** ± 135.1 |
| Treatment group 1-8 (armepavine) | 260.0** ± 56.15 | 524.0* ± 149.3 |
| Treatment group 1-9 (O-methylarmepavine) | 708.0* ± 85.5 | 1114** ± 158.6 |
| Treatment group 1-10 (O-methylarmepavine) | 214.3** ± 14.6 | 321.3** ± 30.3 |
| Negative control group 1-2 | 1098 ± 44.7 | 1769 ± 115.8 |

*p < 0.05
**p < 0.01

The ultromotivities of the mice in treatment groups were significantly more suppressed than that in control groups.

EXAMPLE 2

(Evaluation of Sleep-Enhancing Action)

Actions on thiopental sleep by various compounds were evaluated. Thiopental dissolved in physiological saline was administered intraperitoneally into mice at a dose of 60 mg/kg. 50 mg/kg of neferine hydrochloride (treatment group 2-1, n=9), 50 mg/kg of isoliensinine hydrochloride (treatment group 2-2, n=9), 100 mg/kg of lien tzehsin 2 extract hydrochloride (treatment group 2-3, n=9), only physiological saline (negativity control group, n=6), or 1 mg/kg of diazepam (positive control group, n=9) was administered intraperitoneally into the mice 15 minutes before the thiopental administration. The time when the righting reflex of the mice disappeared after thiopental administration was designated as sleep-induction time, while total sleep time was calculated from the induction time and the time when the righting reflex was restored. The results are summarized in TABLE 3.

TABLE 3

| Test group | Total sleep time (min) |
|---|---|
| Treatment group 2-1 (neferine) | 100 |
| Treatment group 2-2 (isoliensinine) | 120 |
| Treatment group 2-3 (extract 2) | 150 |
| Positive control group (diazepam) | 130 |
| Negative control group (physiological saline) | 20 |

As apparent from the results above, the total sleep times of thiopental sleep were obviously elongated in the administration groups.

EXAMPLE 3

(Evaluation of the Effects on Mental Excitement of the Patients with Integration Ataxia)

The effects of neferine on suppression of the enhancement of ultromotivity by methamphetamine were evaluated.

Fifteen mice were grouped into three groups of five mice, to which 50 mg/kg of neferine hydrochloride (treatment group 3-1), 100 mg/kg of the same (treatment group 3-2), and only physiological saline (negativity control group) were administered respectively intraperitoneally. Methamphetamine (1 mg/kg) was administered 15 minutes after the administration. After administration of methamphetamine, each of the mice was placed in a transparent polycarbonate cage (22.5 cm×33.8 cm×14.0 cm), where the ultromotivity of the mouse was analyzed for 60 minutes by using a locomotor activity analyzer (NS-AS01, Neuroscience Inc.).

The results are summarized as ultromotivity count in TABLE 4.

TABLE 4

| Test group | Ultromotivity (count) |
|---|---|
| Treatment group 3-1 (neferine 50 mg) | 2600 |
| Treatment group 3-2 (neferine 100 mg) | 1800 |
| Negative control group (physiological saline) | 3300 |

As apparent from the results, neferine has an obvious action suppressing the ultromotivity enhancement by methamphetamine, which was not found in the control group, suggesting that neferine is effective in treating mental excitement of the patients with integration ataxia.

EXAMPLE 4

(Evaluation of Antidepressive Action)

Forced swimming tests were conducted according to the method of Porsolt et al. A mouse was placed in a cylindrical glass water tank of 10 cm in diameter and 25 cm in height (water temperature: 23° C.) filled with water to a depth of 10 cm and forced to swim therein. 14 mice were grouped into two groups of seven mice, and 100 mg/kg of neferine hydrochloride (treatment group 4-1) or physiological saline (negativity control group 4-1) was administered intraperitoneally to the mice in each group. Each mouse was forced to swim 15 and 30 minutes after administration, and the immobile times during the 6-minute periods immediately after forced swimming were determined.

The results are shown in TABLE 5 as the average of the seven mice in respective groups.

TABLE 5

| Test group | Immobile time (sec) | |
|---|---|---|
| | After 15 minutes | After 30 minutes |
| Treatment group 4-1 (neferine) | 165 | 170 |
| Negative control group 4-1 (physiological saline) | 265 | 250 |

The immobile times of the treatment group were obviously shortened, compared to that of the negativity control group. The forced swimming test is widely used for evaluation of the pharmacological effects of antidepressants, and thus the results above suggests that neferine has an antidepressive action.

Similar tests were repeated by i.p. administration of 25 mg/kg of armepavine (treatment group 4-2, n=7), 25 mg/kg of O-methylarmepavine (treatment group 4-3, n=6) and physiological saline (negativity control group 4-2, n=5). The significant difference test was conducted according to Dunnett method. The results are summarized in TABLE 6.

TABLE 6

| Test group | Immobile time (sec) after 15 minutes |
|---|---|
| Treatment group 4-2 (armepavine) | 174.5** ± 13.48 |
| Treatment group 4-3 (O-methylarmepavine) | 152.0** ± 14.35 |
| Negative control group 4-2 (physiological saline) | 225.4 ± 9.6 |

**$p < 0.01$

As shown in TABLE 6, the immobile times in the treatment groups were both shortened significantly from that of the control group.

EXAMPLE 5

(Evaluation of Antianxiety Action)

An elevated plus-maze (Neuroscience Inc.) consisting of 2 arms without high walls and 2 arms enclosed by high walls, which were crossing perpendicular to each other, was used for evaluation. A mouse was placed on the platform at the center in a position facing toward an arm enclosed by high walls, and the number of times the mouse entered into both arms and the period of the mouse staying in the arms without walls were determined during a period of 5 minutes. The results were evaluated by the ratios of the number of the mouse entering into the arms with walls with respect to the total number of entering into both arms (%) and by the period of the mouse staying in the arms without walls (%).

The measurements were performed 30 minutes after intraperitoneal administration of mice respectively with 100 mg/kg of neferine hydrochloride (treatment group 5-1, n=5), 100 mg/kg of lien tzehsin extract 2 hydrochloride (treatment group 5-2, n=5) and physiological saline (negativity control group, n=5).

The results are summarized in TABLE 7.

TABLE 7

| Test group | Staying period (%) | Invasion times (%) |
|---|---|---|
| Treatment group 5-1 (neferine) | 33 | 70 |
| Treatment group 5-2 (extract 2) | 19 | 58 |
| Negative control group (physiological saline) | 13 | 47 |

From the results above, the number of the mouse entering into the arms enclosed with walls and the period of the mouse staying in the arms without walls were found to be obviously shortened, compared to those in the negative control group. The results suggest that neferine had an antianxiety action.

EXAMPLE 6

(Evaluation of the Therapeutic Action on Obsessive Compulsive Disorders)

In evaluating glass ball-covering behavior, wood chip for breeding (beta chip) (Oriental Yeast Co., Ltd.) was placed in the transparent cage described in Example 3 to a depth of 5 cm, on which 20 glass balls (diameter: 1.5 cm) were placed evenly.

Twenty-one mice were grouped into three groups of seven mice, to which 25 mg/kg of neferine hydrochloride (treatment group 6-1), 50 mg/kg of the same (treatment group 6-2), and physiological saline (negativity control group) were administered intraperitoneally, respectively. A mouse was placed in the case 15 minutes after administration, and the number of the glass balls not covered with the wood chip was counted by visual observation at an interval of 10 minutes. The number of balls having $2/3$ of the surface thereof being embedded in the wood chip was counted as the criteria for judgment.

The results are shown in TABLE 8 as the average of seven mice.

TABLE 8

| Test group | Number of glass balls not covered with wood chip | | |
|---|---|---|---|
| | After 10 minutes | After 20 minutes | After 30 minutes |
| Treatment group 6-1 (neferine) | 4 | 7 | 10 |
| Treatment group 6-2 (neferine) | 3 | 6 | 9 |
| Negative control group (physiological saline) | 13 | 15 | 17 |

The numbers of balls hidden in treatment groups were all obviously smaller than that of the negativity control group. The test results are known to correlate well to the therapeutic action on obsessive compulsive disorders, indicating that neferine is applicable as a therapeutic drug for obsessive compulsive disorders.

EXAMPLE 7

(Evaluation of Muscle-Relaxing Side Reaction and Motor Coordination)

Tests were performed by using mice administered intraperitoneally with 25 mg/kg of neferine hydrochloride (treatment group 7-1, n=6), 25 mg/kg of liensinine hydrochloride (treatment group 7-2, n=6), and physiological saline (negativity control group, n=6) as well as 5 mg/kg of diazepam (positive control group, n=6) and a rotarod equipment (Ugo Basile, Italy) and a locomotor activity monitoring system (NS-ASO1, Neuroscience Inc.). The rotarod test was performed by placing a mouse on a rod having a diameter of 4 cm rotating at a speed of 8 rpm 15 minutes after drug administration and observing whether the mouse can stay on the rod without falling for three minutes. The individuals that had fallen from the rotating rod in the period of 3 minutes were judged that they are with motor coordination disorder. The mice used in the test were selected from those that did not fall in a preliminary test for three minutes conducted before the test on the same day. In addition, the ultromotivity measurements were performed at an interval of five minutes for 60 minutes, and the ultromotivity results were subjected to a significant difference test (Tukey's method) by using the counts at respective measuring times.

The results are summarized in Table 9.

TABLE 9

| Test group | Number of individuals fallen | Significant difference test of ultromotivity |
|---|---|---|
| Treatment group 7-1 (neferine) | 0 | $P < 0.01$ |
| Treatment group 7-2 (liensinine) | 0 | In declining trend |
| Positive control group (diazepam) | 5 | $P < 0.005$ |
| Negative control group (physiological saline) | 0 | — |

These results indicate that both drugs in treatment groups exert a sedative action without inducing a muscle-relaxing action or motor coordination disorder.

EXAMPLE 8

(Evaluation of Catalepsy)

Catalepsy tests were performed by using mice administered with 200 mg/kg of lien tzehsin extract 1 hydrochloride (treatment group 8-1, n=6) and 100 mg/kg of extract 2 hydrochloride (treatment group 8-2, n=6), 100 mg/kg of neferine (treatment group 8-3, n=6), 25 mg/kg armepavine (treatment group 8-4, n=6), and 25 mg of O-methylarmepavine (treatment group 8-5, n=6). The mice in the treatment group 8-1 were fed with laboratory chow containing 10% lien tzehsin extract 1 instead of common chow.

The mice except in the treatment group 8-1 were administered intraperitoneally with respective drugs. After 15 minutes from administration, rods of 5.5 cm in height were supplied respectively to the six mice in feeding case for holding, and the number of mice which remained there holding the rod for 30 seconds (indicated by */6) was counted and used as catalepsy positivity.

Physiological saline (negativity control group, n=6) and 1 mg/kg of a drug haloperidol (positive control group, n=6) were used as controls respectively.

As a result, the catalepsy positivities were (0/6) in negativity control group, (0/6) in treatment groups 8-1 to 8-5, and (6/6) in the positive control group. Namely, no catalepsy was observed in the mice of treatment groups.

The results indicate that the drugs used in treatment groups do not induce an adverse reaction of extrapyramidal tract disorders.

EXAMPLE 9

(Preparative Examples)

(A) Preparation of Tablet

A mixture of 4 g of neferine, 400 g of oligosaccharide, 30 g of calcium phosphate, and 170 g of sucrose fatty acid ester was blended in a V-type mixer for 20 minutes and then compressed in a rotary press under a pressure of 800 kgf/cm$^2$, to give 100-mg tablets.

(B) Preparative of Drinkable Preparation 0.1 g of neferine and 20 g of boiled extract of jasmine tea were dissolved in 970 cc of water, and the solution was then filtered.

(C) Preparation of Capsule 2 g of neferine previously crushed to an average grain size of about 100 micron in a ball mill and 50 g of lactose were mixed well and the mixture was encapsulated with gelatin to give capsules.

(D) Preparative of Powdered Formulation:

2 g of neferine and 20 g of American ginseng extract, 10 g of castor oil, and 5 g of Hivis Wako (Wako Pure Chemical Industries) were blended. The mixture was dropped onto a rotating disk, to give powders having a diameter of approximately 30 micron.

The benzylisoquinoline and bisbenzylisoquinoline derivatives derived from lien tzehsin of which the activity was found in the present invention exhibit no toxicity to the living body and may provide safer therapeutic products effective in preventing central nervous system diseases. They can also be used in health foods and health beverages.

Further, the psychotropic drug according to the present invention is extremely advantageous as it has smaller adverse reactions than conventional drugs and shows activities in a wider range of neurotropic actions.

What is claimed is:

1. A method for alleviating depression, comprising administering effective amounts to a patient in need thereof, a purified benzylisoquinoline compound selected from the group consisting of armepavine and O-methylarmepavine.

2. The method according to claim 1, wherein said compound is administered orally as part of a health food containing said compound.

3. The method according to claim 2, wherein the health food is a beverage or drinkable preparation.

* * * * *